United States Patent
Kwon et al.

(10) Patent No.: US 8,036,753 B2
(45) Date of Patent: Oct. 11, 2011

(54) STIMULATION MODE FOR COCHLEAR IMPLANT SPEECH CODING

(75) Inventors: Bomjun Kwon, Aurora, CO (US); Chris van den Honert, Aurora, CO (US)

(73) Assignee: Cochlear Limited, Lane Cove, NSW (AU)

( * ) Notice: Subject to any disclaimer, the term of this patent is extended or adjusted under 35 U.S.C. 154(b) by 890 days.

(21) Appl. No.: 11/030,980

(22) Filed: Jan. 10, 2005

(65) Prior Publication Data

US 2005/0177205 A1 Aug. 11, 2005

Related U.S. Application Data

(60) Provisional application No. 60/535,210, filed on Jan. 9, 2004.

(51) Int. Cl.
*A61N 1/18* (2006.01)

(52) U.S. Cl. .............................................. 607/57; 607/58

(58) Field of Classification Search ............... 607/55–57
See application file for complete search history.

(56) References Cited

U.S. PATENT DOCUMENTS

| | | | |
|---|---|---|---|
| 4,284,856 A | 8/1981 | Hochmair et al. | |
| 4,515,158 A * | 5/1985 | Patrick et al. | 607/57 |
| 4,593,696 A * | 6/1986 | Hochmair et al. | 607/57 |
| 4,813,417 A | 3/1989 | Soli et al. | |
| 4,823,795 A | 4/1989 | van den Honert | |
| 5,095,904 A * | 3/1992 | Seligman et al. | 607/57 |
| 5,531,774 A * | 7/1996 | Schulman et al. | 607/56 |
| 5,597,380 A | 1/1997 | McDermott et al. | |
| 5,776,172 A | 7/1998 | Schulman et al. | |
| 5,876,443 A | 3/1999 | Hochmair et al. | |
| 5,999,859 A | 12/1999 | Jolly | |
| 6,219,580 B1 | 4/2001 | Faltys et al. | |
| 6,272,382 B1 | 8/2001 | Faltys et al. | |
| 6,289,247 B1 * | 9/2001 | Faltys et al. | 607/57 |
| 6,321,125 B1 | 11/2001 | Kuzma | |
| 6,390,971 B1 | 5/2002 | Adams et al. | |
| 6,480,820 B1 | 11/2002 | Clopton et al. | |
| 6,572,531 B2 | 6/2003 | Zilberman et al. | |
| 6,604,283 B1 | 8/2003 | Kuzma | |
| 6,611,717 B1 * | 8/2003 | Clark et al. | 607/56 |
| 6,732,073 B1 | 5/2004 | Kluender et al. | |
| 6,778,858 B1 | 8/2004 | Peeters | |
| 6,915,166 B1 | 7/2005 | Stecker et al. | |
| 6,920,360 B2 | 7/2005 | Lee et al. | |
| 7,082,332 B2 | 7/2006 | Blamey et al. | |

(Continued)

FOREIGN PATENT DOCUMENTS

AU 2001265692 1/2002

(Continued)

OTHER PUBLICATIONS

Australian Office Action dated Apr. 3, 2009 for AU 2005200067.

(Continued)

*Primary Examiner* — Carl H Layno
*Assistant Examiner* — Paula J Stice (57) ABSTRACT

A method of stimulating an auditory nerve to produce a percept in response to a detected sound signal. At least one characteristic of the sound signal is identified, and a stimulation mode is selected based on the identified characteristic. The selected stimulation mode is then used for stimulating the auditory nerve to convey the sound signal to the prosthesis recipient. Multiple characteristics of the detected sound signal may be assigned distinct stimulation modes.

24 Claims, 3 Drawing Sheets

U.S. PATENT DOCUMENTS

| | | | |
|---|---|---|---|
| 7,103,417 B1 | 9/2006 | Segel et al. | |
| 7,251,530 B1 | 7/2007 | Overstreet et al. | |
| 7,292,892 B2 | 11/2007 | Litvak et al. | |
| 7,729,775 B1 | 6/2010 | Saoji et al. | |
| 2003/0135247 A1 | 7/2003 | Zierhofer | |
| 2003/0171786 A1 | 9/2003 | Blamey et al. | |
| 2004/0015210 A1* | 1/2004 | Clark et al. | 607/57 |
| 2004/0136556 A1* | 7/2004 | Litvak et al. | 381/316 |
| 2005/0010267 A1 | 1/2005 | Ibrahim | |
| 2005/0187592 A1* | 8/2005 | Seligman et al. | 607/57 |
| 2005/0192646 A1 | 9/2005 | Grayden et al. | |
| 2006/0080087 A1 | 4/2006 | Vandali et al. | |
| 2006/0212095 A1 | 9/2006 | Wolfe et al. | |
| 2006/0265061 A1 | 11/2006 | Kwon et al. | |
| 2008/0234783 A1 | 9/2008 | van den Honert | |

FOREIGN PATENT DOCUMENTS

| | | |
|---|---|---|
| EP | 0661905 | 12/2002 |
| WO | 01/99470 | 12/2001 |
| WO | 2004021363 | 3/2004 |
| WO | 2005057983 | 6/2005 |

OTHER PUBLICATIONS

International Search Report for PCT/US2008/057690 dated Aug. 29, 2008.

Robles et al., "Mechanics of the Mamalian Cochlean," Physiological Review, Jul. 3, 2001, pp. 1305-1352, vol. 81, No. 3.

Written Opinion for PCT/US2008/057690 dated Aug. 29, 2008.

International Preliminary Examining Authority, "International Preliminary Report on Patentability," issued in connection with International Patent Application No. PCT/US2008/057690, on Feb. 27, 2009 (7 pages).

European Search Report, "Extended European Search Report," issued in connection with European Patent Application No. 08744124.2, on May 20, 2010 (6 pages).

U.S. Appl. No. 11/335,563, Office Action mailed on Jul. 17, 2008, 11 Pages.

U.S. Appl. No. 11/335,563, Office Action mailed on Mar. 9, 2010, 12 Pages.

U.S. Appl. No. 11/335,563, Office Action mailed on Oct. 15, 2010, 16 Pages.

U.S. Appl. No. 11/335,563, Office Action mailed on Jul. 20, 2009, 7 Pages.

U.S. Appl. No. 11/335,563, Office Action mailed on Jan. 23, 2009, 8 Pages.

U.S. Appl. No. 11/723,696, Office Action mailed on Jan. 27, 2010, 14 Pages.

U.S. Appl. No. 11/723,696, Office Action mailed on Jul. 8, 2009 ,15 Pages.

U.S. Appl. No. 11/723,696, "Office Action", Nov. 26, 2010 , 20.

* cited by examiner

FIG. 1

STIMULATION MODE FOR COCHLEAR IMPLANT SPEECH CODING

CROSS-REFERENCE TO RELATED APPLICATIONS

The present application claims priority from U.S. Provisional Patent Application No. 60/535,210 filed on 9 Jan. 2004, the content of which is incorporated herein by reference.

BACKGROUND

1. Field of the Invention

The present invention relates to electrical stimulation of the auditory nerve by an implanted prosthesis in response to detected sound, in a manner which produces a percept which conveys an increased amount of information regarding that sound to the recipient of the prosthesis.

2. Related Art

Cochlear implants have been developed to assist people who are profoundly deaf or severely hearing impaired, by enabling them to experience hearing sensation representative of the natural hearing sensation. For most such individuals the hair cells in the cochlea, which normally function to transduce acoustic signals into nerve impulses which are interpreted by the brain as sound, are absent or have been destroyed. The cochlear implant therefore bypasses the hair cells to directly deliver electrical stimulation to the auditory nerves with this electrical stimulation being representative of the sound.

Cochlear implants have traditionally consisted of two parts, an external speech processor unit and an implanted receiver/stimulator unit. The external speech processor unit has been worn on the body of the user and its main purpose has been to detect the external sound using a microphone and convert the detected sound into a coded signal through an appropriate speech processing strategy.

This coded signal is then sent to the receiver/stimulator unit which is implanted in the mastoid bone of the user, via a transcutaneous link. The receiver/stimulator unit processes the coded signal into a series of stimulation sequences which are then applied directly to the auditory nerve via a series or an array of electrodes positioned within the cochlea. One such cochlear implant is set out in U.S. Pat. No. 4,532,930, the contents of which are incorporated herein by reference.

Several modes or techniques of stimulation have been proposed. One such mode, referred to generally as bipolar stimulation, typically comprises passing current between a pair of electrodes, which in general may be any two electrodes of the electrode array of the implant. All other electrodes in the array are kept 'floating' or inactive during such a stimulation. Bipolar (BP) stimulation is also used in a specific sense to refer to stimulation by passing current between adjacent electrodes of the array. A bipolar+1 (BP+1) stimulation mode involves passing a current between two electrodes which are separated by one inactive electrode. Similarly, a bipolar+n (BP+n) stimulation mode involves passing current between two electrodes which are separated by n inactive electrodes.

Another mode of stimulation is referred to as monopolar (MP) stimulation, which involves passing current between an electrode of the implanted array and an electrode outside the cochlea (known as an extra-cochlear electrode or ECE) which for example may be mounted on the receiver/stimulator unit.

Yet another mode of stimulation, known as variable bipolar stimulation, involves use of a single electrode of the implanted array as the return electrode for all stimulations, regardless of the other active electrode.

Still another mode of stimulation, known as common ground (CG) stimulation, involves applying current via one electrode of the electrode array, with all other electrodes of the array being grounded and thus providing a return path for the stimulation.

With improvements in technology it is possible that the external speech processor and implanted stimulator unit may be combined to produce a totally implantable cochlear implant unit that is capable of operating, at least for a period of time, without the need for any external device. In such a device, a microphone would be implanted within the body of the user, for example in the ear canal or within the stimulator unit, and sounds would be detected and directly processed by a speech processor within the stimulator unit, with the subsequent stimulation signals delivered without the need for any transcutaneous transmission of signals. Such a device would, however, still have the capability to communicate with an external device when necessary, particularly for program upgrades and/or implant interrogation, and if the operating parameters of the device required alteration.

Typically, following the surgical implantation of a cochlear implant, the recipient must have the implant fitted or customised to conform with the specific demands of that recipient. This procedure is usually referred to as "mapping" and is the process of measuring and controlling the amount of electrical current delivered to the cochlea, and determining the manner in which the electrical current should be delivered. The mapping process leads to the creation of a program or map that ensures stimulation from the implant provides a patient with comfortable and useful auditory perception, and is essential in ensuring that the recipient receives maximum benefit from the cochlear implant. As the implant system is designed to present acoustic information, in particular speech, to a patient in a useable form, the initial aim of the mapping process is to optimise the information provided for a particular patient.

The mapping process includes identifying a stimulation mode which produces the best speech percept for the recipient. As noted previously herein, there are several possible modes or techniques of stimulation, and at the time of mapping a selection is made as to the most appropriate stimulation mode based on the percept produced. That stimulation mode is then fixed unless and until clinical remapping should become necessary.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY

According to an aspect of a first embodiment, the present invention provides a method of stimulating an auditory nerve to produce a percept in response to a detected sound signal, the method comprising:

identifying at least one characteristic of the sound signal; and selecting one of a plurality of stimulation modes for stimulating the auditory nerve to convey the sound signal to the prosthesis recipient, said selection being based on said identified characteristic.

In some embodiments of the invention, at least two characteristics of the sound signal are identified. Such embodiments preferably further comprise selecting a distinct stimulation mode for each identified characteristic, such that a unique stimulation mode is used to apply each identified characteristic to the auditory nerve.

According to an aspect of a second embodiment, the present invention provides a hearing prosthesis operable to stimulate an auditory nerve to produce a percept in response to a detected sound signal, the prosthesis comprising:

means for identifying at least one characteristic of the sound signal; and means for selecting one of a plurality of stimulation modes for stimulating the auditory nerve to convey the sound signal to the prosthesis recipient, said selection being based on said identified characteristic.

According to an aspect of a third embodiment, the present invention provides a speech processor for processing detected sound into stimulation signals, the speech processor comprising:

means for identifying at least one characteristic of the detected sound; and means for selecting one of a plurality of stimulation modes for stimulating the auditory nerve to convey the sound signal to the prosthesis recipient, said selection being based on said identified characteristic.

According to an aspect of a fourth embodiment the present invention provides a computer program for processing detected sound into stimulation signals, comprising:

code for identifying at least one characteristic of the detected sound; and code for selecting one of a plurality of stimulation modes for stimulating the auditory nerve to convey the sound signal to the prosthesis recipient, said selection being based on said identified characteristic.

The computer program preferably further comprises code for generating commands for stimulations to be applied by at least one electrode in accordance with said one of the plurality of stimulation modes. The commands may comprise radio frequency (RF) frames for transcutaneous transmission to an implanted receiver/stimulator unit.

According to an aspect of a fifth embodiment, the present invention provides a computer program element comprising computer program code means to make a computer execute a procedure for processing detected sound into stimulation signals, comprising:

computer program code means for identifying at least one characteristic of the detected sound; and computer program code means for selecting one of a plurality of stimulation modes for stimulating the auditory nerve to convey the sound signal to the prosthesis recipient, said selection being based on said identified characteristic.

The computer program preferably further comprises code for generating commands for stimulations to be applied by at least one electrode in accordance with said one of the plurality of stimulation modes. The commands may comprise radio frequency (RF) frames for transcutaneous transmission to an implanted receiver/stimulator unit.

According to an aspect of a sixth embodiment the present invention provides a computer readable medium having recorded thereon a computer program in accordance with the fourth aspect.

According to an aspect of another embodiment of the present invention, there is provided a method of programming operation of a multi-channel cochlear prosthesis, the method comprising the steps of:

selecting a set of measurable incoming sound characteristics;

selecting a set of available stimulation modes; and determining an instruction set for each of the selected available stimulation modes to be operable according to measures taken from the selected set of measurable incoming sound characteristics.

In embodiments of the invention in which a plurality of stimulation modes are used to apply stimulations to the auditory nerve representing distinct characteristics of the sound signal, a pitch map is preferably used in generating the stimulations so as to allow for differing pitch perceptions of stimulations in each distinct stimulation mode.

In embodiments of any of the preceding aspects of the invention, the at least one identified characteristic of the sound signal may comprise one or more of:

one or more unique sound sources, such as one or more human voices, identified in the presence of background noise;

time trajectory of a fundamental frequency (F0) of a human voice;

time trajectory of a first formant frequency (F1) of a human voice;

time trajectory of a second formant frequency (F2) of a human voice;

a quantitative metric indicating a degree of voicing of a human voice;

a quantitative metric indicating a degree of nasality of a human voice;

a quantitative metric indicating a fricative degree of a human voice; and a quantitative metric indicating an abruptness of a human voice.

In embodiments of any of the preceding aspects of the invention, the plurality of stimulation modes may comprise two or more modes selected from:

the monopolar family of stimulation modes;

the bipolar family of stimulation modes;

a tripolar mode utilizing a current flowing from one electrode to two adjacent electrodes situated either side of the one electrode; and a double monopolar mode utilizing current flowing from two intra-cochlear electrodes to one or more extra-cochlear electrodes.

It is to be appreciated that, in general, the plurality of stimulation modes may be selected to be any stimulation mode involving current flow among electrodes.

BRIEF DESCRIPTION OF THE DRAWINGS

By way of example only, preferred embodiments of the invention will be described with reference to the accompanying drawings, in which.

DETAILED DESCRIPTION

Figure 1:
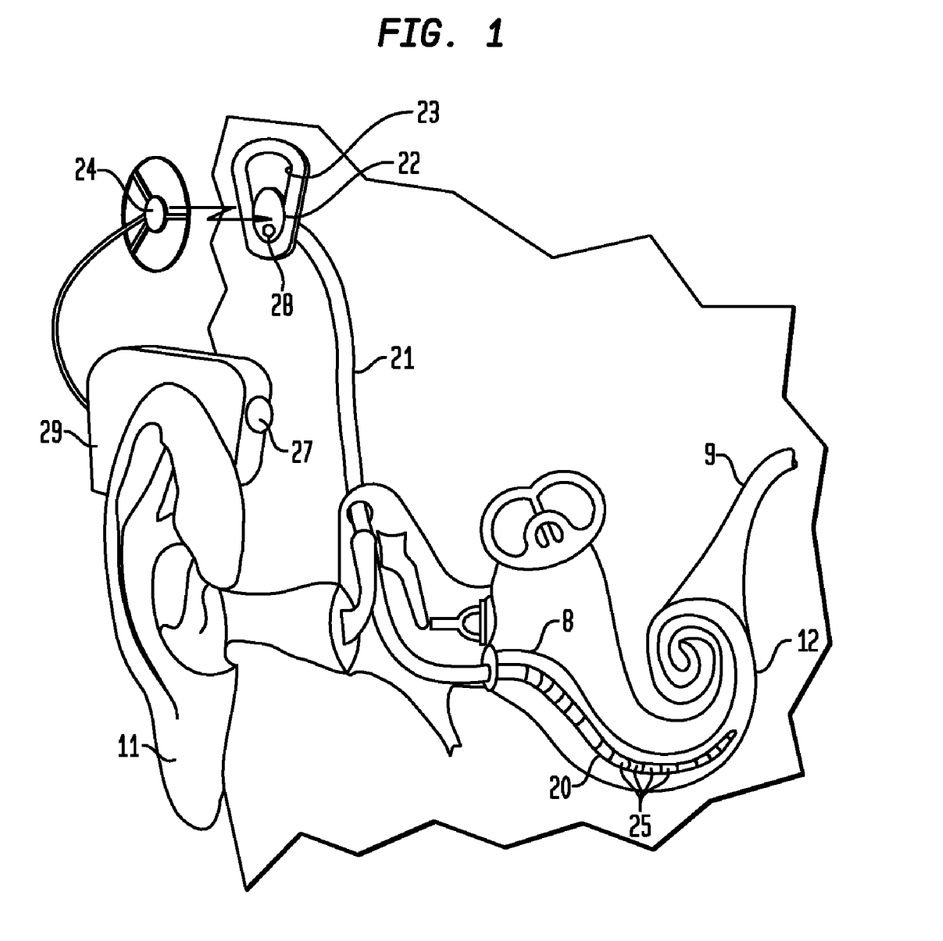
FIG. 1 is a pictorial representation of a cochlear implant system.

Before describing the features of the present invention, it is appropriate to briefly describe the construction of one type of known cochlear implant system with reference to FIG. 1.

Known cochlear implants typically consist of two main components, an external component including a speech processor 29, and an internal component including an implanted receiver and stimulator unit 22. The external component includes an on-board microphone 27. The speech processor 29 is, in this illustration, constructed and arranged so that it can fit behind the outer ear 11. Alternative versions may be worn on the body. Attached to the speech processor 29 is a transmitter coil 24 which transmits electrical signals to the implanted unit 22 via an RF link.

The implanted component includes a receiver coil 23 for receiving power and data from the transmitter coil 24. A cable 21 extends from the implanted receiver and stimulator unit 22 to the cochlea 12 and terminates in an electrode array 20. The signals thus received are applied by the array 20 to the basilar membrane 8 thereby stimulating the auditory nerve 9. The operation of such a device is described, for example, in U.S. Pat. No. 4,532,930.

The sound processor 29 of the cochlear implant can perform an audio spectral analysis of the acoustic signals and outputs channel amplitude levels. The sound processor 29 can also sort the outputs in order of magnitude, or flag the spectral maxima as used in the SPEAK strategy developed by Cochlear Ltd. Other speech processing strategies which may be used include ACE (advanced combination encoders).

In the absence of a visual cue, currently only a small subset of cochlear implant recipients have a listening ability comparable to that of people with normal hearing. In adverse listening conditions, such as in the presence of background noise, almost no cochlear implant recipients have a listening ability comparable to that of people with normal hearing. It has now been recognised that this indicates that speech information is not sufficiently available to cochlear implant recipients through their speech processor operating under present speech encoding strategies. Further, current speech coding strategies appear to have reached asymptotes in user's performance, because recent research attempts to improve the user's performance with existing devices involve either fine-tuning the clinical map with parameter adjustments based on performance and the recipient's preference, or adjustments to front-end processing of input signals.

However, in accordance with the present invention, signals can be encoded in multiple stimulation modes and the resulting "complex" auditory percept due to the multiple modes can be applied to speech coding. The present invention thus adds another dimension of leverage to speech coding strategy. By making some portion of stimulation distinct from another portion of stimulation by using a different stimulation mode, the present invention provides further opportunities to enhance encoding of speech features (e.g., formant transition), encoding of prosodic features (intonations and tones) and processing of multiple auditory input streams (speech in the background of alarming sound, or two independent speech inputs).

Multiple stimulation modes may be used to increase informational channels and to improve the sophistication of speech information through the speech processing. The present invention recognises that, for example, bipolar mode and monopolar mode each induce a distinct auditory percept, and that a change between multiple stimulation modes or the mixture of modes may be used to create a distinct and salient percept that represents information of dynamic speech or other auditory percepts. Due to this distinct sound percept between stimulation modes, sound streams simultaneously presented by a distinct mode can each carry a distinct percept. This distinct percept may lead to patients' improvement in intensity discrimination, and may also lead to an improved ability to detect and track modulations in intensity and frequency in the mixed mode condition.

Accordingly, by selecting a set of measurable incoming sound characteristics and taking measures of those characteristics, instruction sets for each available stimulation mode can be determined. The available stimulation modes can themselves be a set of selected stimulation modes. A multi-channel cochlear prosthesis thus programmed provides for operation of each stimulation mode in accordance with the respective instruction set, which are in turn based on the measures taken from the measurable characteristics.

Figure 2:
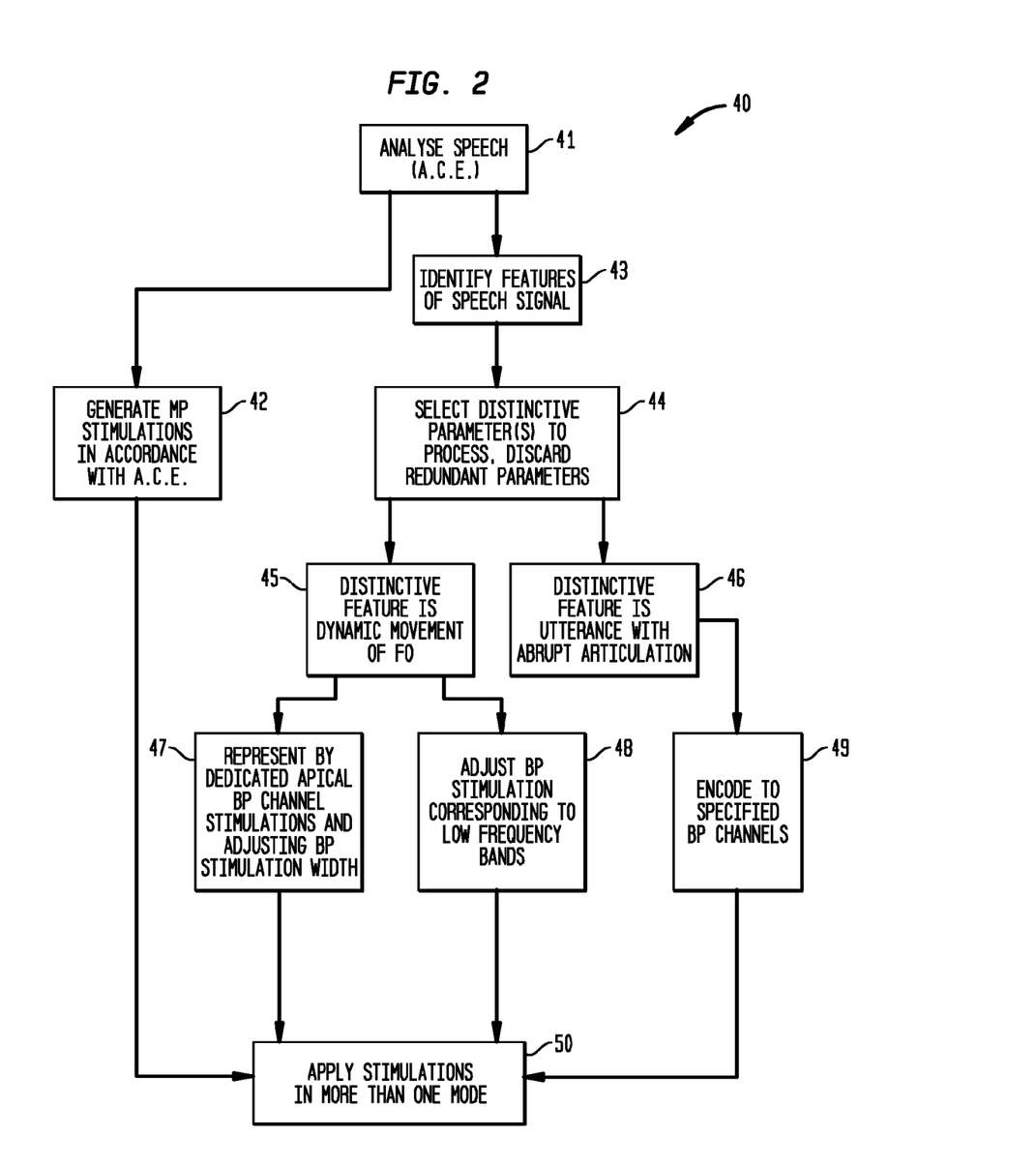
FIG. 2 illustrates a stimulation generation process in accordance with one embodiment of the present invention.

FIG. 2 illustrates a process 40 of producing a multiple mode stimulation in accordance with the present invention, which may be implemented by an appropriately programmed multi-channel cochlear prosthesis. In general, the process 40 uses multiple stimulation modes from a set of available stimulation modes to represent a single source of speech sound, for the purpose of the selective emphasis on distinctive features of speech, being measurable characteristics of the speech sound. Such a process is most effective if there is one speech signal without a distortion or a perturbation from background noise. Considering FIG. 2 in more detail, process 40 includes an initial step 41 of processing a speech signal using existing processing strategies, such as advanced combination encoders (ACE). At step 42 monopolar stimulation pulses are generated in accordance with the traditional ACE strategy.

In addition, at step 43 a set of features or measurable characteristics of the input speech signal are analysed. There is a large range of choice as to how many features are chosen and through which methods those features are identified. In the present embodiment, the set of features analysed comprises: time trajectory of the fundamental frequency (F0), first and second formant frequencies (F1 and F2) and their time trajectories, and quantitative metrics indicating the degrees of voicing, nasal, fricative, and burst strength. At step 44, a selection is made as to which of the identified parameters is to be processed as a distinctive feature. This step is necessary because some of the parameters analysed in step 43 may be redundant or may interact with each other. For example, if the voicing is indicated low for a portion of waveform, the analysis of fundamental frequency is not critical.

In the embodiment shown in FIG. 2, the distinctive parameters selected in step 44 comprise the dynamic movement of F0 and an utterance with an abrupt articulation. Additional or alternative distinctive features may be selected. At steps 45 and 46, the distinctive features selected in step 44 are processed using BP modes (with a varying degree of electrode separation to achieve more natural representation of the distinctive features). In the present embodiment, the dynamic movement of F0 can be represented by dedicated apical BP channels, by adjusting of the width of BP stimulation according to the input, as set out in step 47. Alternatively, the dynamic movement of F0 can be represented by adjusting the relative contribution of BP stimulation to the existing MP stimulation corresponding to low frequency bands, as illustrated at step 48.

Further, at step 49 a pattern of BP stimulation is assigned to represent the distinctive speech feature of the utterance with an abrupt articulation (usually corresponding to stop consonants). In the embodiment shown in FIG. 2, this distinctive feature is encoded at step 49 to a specified range of BP channels, however in alternate embodiments this distinctive feature may be encoded to a specified range of BP channels with some contribution from MP channels as well.

Due to differing pitch percepts which are produced by differing stimulation modes, generation of the instructions sets for the respective stimulation signals at steps 42, 47 or 48, and 49 includes using a stimulation mode pitch map to improve pitch matching between each stimulation mode. The stimulation mode pitch map is obtained by psychophysiological testing of the recipient. While the bipolar and monopolar stimulation modes are being used by cochlear implants commercially available at present, other stimulation modes involving current flow among electrodes may be used to effect in the present invention. For example, a tripolar stimulation mode, utilizing a current flowing from one electrode to the two adjacent electrodes on both sides, may be used. Similarly, a double monopolar stimulation mode may be used, in which a current flows from two intra-cochlear electrodes to one or more extra-cochlear electrodes.

The multiple modes of stimulation generated at steps 42, 47 or 48, and 49 are then applied to the auditory nerve at step 50.

In alternate embodiments of the present invention the specifics of implementation may vary, for example depending on the patient's preference, auditory experience, and device limitation, with a view to increasing the intelligibility of encoded speech.

Figure 3:
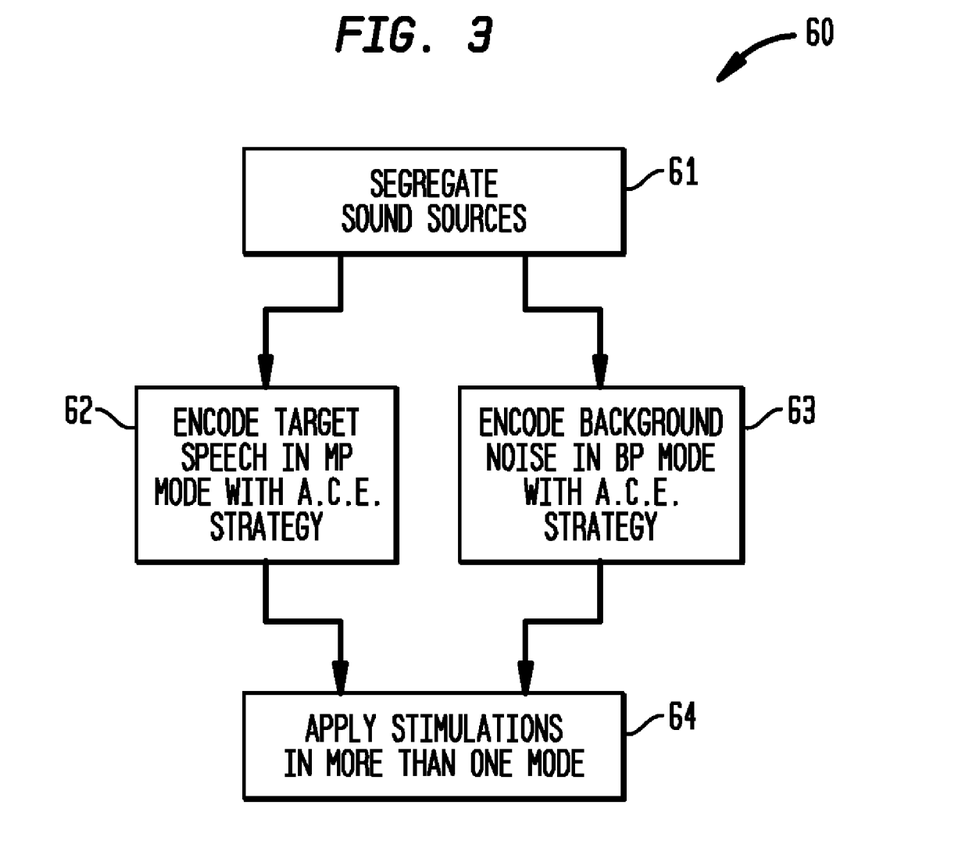
FIG. 3 illustrates a stimulation generation process of another embodiment of the invention.

FIG. 3 illustrates a process 60 in accordance with an alternate embodiment of the present invention. This process assigns a unique stimulation mode to represent each source of speech sounds, for the purpose of carrying multiple streams of speech through perceptually more independent channels. In contrast to the embodiment shown in FIG. 2, process 60 does not attempt to analyse distinctive features of a single speech source to utilize multiple stimulation modes, but instead delivers each of a plurality of signals in a unique stimulation mode. Therefore, this approach applies to the case where a listener tries to understand a target speech with a background of other sounds. For instance, the target may be spatially separate from the background.

Considering FIG. 3 in more detail, process 60 comprises an initial step 61 of segregating sound sources. This step may be achieved by locating two microphones in such a way that one directs to the target and the other to the background. Alternatively, signal processing strategies may enable a single sound signal to be processed so as to segregate a particular sound source from background noise. At step 62 a traditional coding strategy, such as ACE, is used to encode the target speech in the MP mode. At step 63 a traditional coding strategy, such as ACE, is used to encode the background in the BP mode. Once again, generation of the stimulation signals at steps 63 and 64 includes using a stimulation mode pitch map to improve pitch matching between each stimulation mode. At step 64 the stimulations generated in a plurality of stimulation modes at steps 62 and 63 are applied to the auditory nerve.

In such embodiments, the two "streams" of input sound encoded in different modes are expected to carry sound information of each relatively less interference because they are transmitted via perceptually different channels. Therefore, patients may be better able to perceptually separate them, and may be able to understand the target speech better. It is also possible that patients may still identify the background sounds concurrently with the target identification, depending on the patient's ability to divide and manage multiple attentions. This concurrent identification, which almost all normal hearing listeners are to a certain degree capable of, but currently almost impossible through any of existing cochlear implant speech processing, may provide an invaluable potential benefit for patients. Such advantages will be dependent not only on the stimulations applied but also on the individual's psychophysiology.

Embodiments of the invention such as that shown in FIG. 2 share some similarities with speech extraction coding strategies such as F0/F1, F0/F1/F2, or MPEAK, in attempting to emphasize specific speech features. However, the embodiment of FIG. 2 differs from such coding strategies in that the primary method of signal delivery will still be based on conventional pulsatile sampling strategies, such as continuous interleaved sampling (CIS), while additional manipulation with stimulation mode selection will be used to supplement the information representation by sampling strategies.

Further, specific implementations of the present invention will be dependent on each device due to hardware limitations. For example, while the Nucleus 24™ system of Cochlear Ltd can implement MP and BP stimulation, the Nucleus 22™ device of Cochlear Ltd does not have extracochlear electrodes, and thus stimulation modes will be manipulated with only the BP-family modes (BP, BP+1, BP+2, etc).

Embodiments of the present invention may provide for improved speech recognition in a noisy environment, by providing patients a more informative percept of speech. Embodiments of the invention may also lead to an improvement in sound quality provided by the implant, thus leading to better identification of a speaker or a speaker's gender (which many patients presently have difficulties identifying), to better prosodic identification (ie, following "emotion" in the voice), and to improved music perception by way of finer frequency modulation representation.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A method of stimulating an auditory nerve to produce a percept in response to a received sound signal, the method comprising:

analyzing a plurality of measurable characteristics of the received sound signal using a processor;

automatically selecting at least one distinctive characteristic of the plurality of measurable characteristics based on the analyzing;

generating a first stimulation signal for representing the selected at least one distinctive characteristic using a first stimulation mode; and generating a second stimulation signal for the received sound signal using a second stimulation mode that is different from the first stimulation mode; wherein each of the first and second stimulation mode specify a different arrangement of electrodes for current flow between the arrangement of electrodes; and applying the first and second stimulation signals to the auditory nerve.

2. The method of claim 1, wherein selecting at least one of the plurality of measurable characteristics comprises selecting at least two measurable characteristics of the sound signal.

3. The method of claim 2, further comprising selecting a distinct stimulation mode for each selected measurable characteristic, such that a unique stimulation mode is used to apply each identified measurable characteristic to the auditory nerve.

4. The method of claim 1, wherein generating a first stimulation signal comprises generating a stimulation signal for the first stimulation mode with reference to a pitch map to allow for differing pitch perceptions of stimulations in each distinct stimulation mode.

5. The method of claim 1, wherein the plurality of measurable characteristics of the sound signal comprises at least two of:
   one or more unique sound sources identified in the presence of background noise;
   time trajectory of a fundamental frequency (F0) of a human voice;
   time trajectory of a first formant frequency (F1) of a human voice;
   time trajectory of a second formant frequency (F2) of a human voice;
   a quantitative metric indicating a degree of voicing of a human voice;
   a quantitative metric indicating a degree of nasality of a human voice;
   a quantitative metric indicating a fricative degree of a human voice; and
   a quantitative metric indicating an abruptness of a human voice.

6. The method of claim 1, wherein the plurality of stimulation modes comprises at least one of:
   a monopolar stimulation mode;
   a bipolar stimulation mode;
   a tripolar mode utilizing a current flowing from one electrode to two adjacent electrodes situated either side of the one electrode; and
   a double monopolar mode utilizing current flowing from two intra-cochlear electrodes to one or more extra-cochlear electrodes.

7. A hearing prosthesis operable to stimulate an auditory nerve to produce a percept in response to a received sound signal, the prosthesis comprising:
   means for analyzing a plurality of measurable characteristics of the received sound signal;
   means for automatically selecting at least one distinctive characteristic of the sound signal based on the analyzing by the means for analyzing;
   means for generating a first stimulation signal for representing the selected at least one measurable characteristic using a first stimulation mode;
   means for generating a second stimulation signal for the received sound signal using a second stimulation mode that is different from the first stimulation mode; wherein each of the first and second stimulation mode specify a different arrangement of electrodes for current flow between the arrangement of electrodes; and
   means for applying the first and second stimulation signals to the auditory nerve.

8. The hearing prosthesis of claim 7, wherein the means for identifying is operable to identify at least two measurable characteristics of the sound signal.

9. The hearing prosthesis of claim 8, wherein the means for selecting is operable to select a distinct stimulation mode for each identified measurable characteristic, such that a unique stimulation mode is used to apply each identified measurable characteristic to the auditory nerve.

10. The hearing prosthesis of claim 7, further comprising means for generating stimulations in each mode with reference to a pitch map to allow for differing pitch perceptions of stimulations in each distinct stimulation mode.

11. The hearing prosthesis of claim 7, wherein the plurality of measurable characteristic of the sound signal comprises at least two of:
   one or more unique sound sources identified in the presence of background noise;
   time trajectory of a fundamental frequency (F0) of a human voice;
   time trajectory of a first formant frequency (F1) of a human voice;
   time trajectory of a second formant frequency (F2) of a human voice;
   a quantitative metric indicating a degree of voicing of a human voice;
   a quantitative metric indicating a degree of nasality of a human voice;
   a quantitative metric indicating a fricative degree of a human voice; and
   a quantitative metric indicating an abruptness of a human voice.

12. The hearing prosthesis of claim 7, wherein the plurality of stimulation modes comprises at least one of:
   a monopolar stimulation mode;
   a bipolar stimulation mode;
   a tripolar mode utilizing a current flowing from one electrode to two adjacent electrodes situated either side of the one electrode; and
   a double monopolar mode utilizing current flowing from two intra-cochlear electrodes to one or more extra-cochlear electrodes.

13. A speech processor for processing a received sound signal into stimulation signals, the speech processor comprising:
   means for analyzing a plurality measurable characteristics of the received sound signal;
   means for automatically selecting at least one distinctive characteristic of the detected sound signal based on the analyzing by the means for analyzing;
   means for generating a first stimulation signal for representing a selected at least one dominant characteristic using a first stimulation mode;
   means for generating a second stimulation signal for the received sound signal using a second stimulation mode that is different from the first stimulation mode; wherein each of the first and second stimulation mode specify a different arrangement of electrodes for current flow between the arrangement of electrodes; and
   means for applying the first and second stimulation signals to the auditory nerve.

14. The speech processor of claim 13, wherein the means for identifying is operable to identify at least two measurable characteristics of the sound signal.

15. The speech processor of claim 14, wherein the means for selecting is operable to select a distinct stimulation mode for each identified measurable characteristic, such that a unique stimulation mode is for applying each identified measurable characteristic to the auditory nerve.

16. The speech processor of claim 13, further comprising means for generating stimulation signals in each mode with reference to a pitch map to allow for differing pitch perceptions of stimulations in each distinct stimulation mode.

17. The speech processor of claim 13, wherein the plurality of measurable characteristics of the sound signal comprises at least two or more of:
   one or more unique sound sources identified in the presence of background noise;

time trajectory of a fundamental frequency (F0) of a human voice;

time trajectory of a first formant frequency (F1) of a human voice;

time trajectory of a second formant frequency (F2) of a human voice;

a quantitative metric indicating a degree of voicing of a human voice;

a quantitative metric indicating a degree of nasality of a human voice;

a quantitative metric indicating a fricative degree of a human voice; and a quantitative metric indicating an abruptness of a human voice.

18. The speech processor of claim 13, wherein the plurality of stimulation modes comprises at least one of:

a monopolar stimulation mode;

a bipolar stimulation mode;

a tripolar mode utilizing a current flowing from one electrode to two adjacent electrodes situated either side of the one electrode; and a double monopolar mode utilizing current flowing from two intra-cochlear electrodes to one or more extra-cochlear electrodes.

19. A non-transitory computer readable medium having recorded thereon, a computer program processing detected sound into stimulation signals, comprising:

code for analyzing a plurality of measurable characteristics of the received sound signal;

code for automatically selecting at least one dominant characteristic of the detected sounds based on the analyzing;

code for generating a first stimulation signal for representing the selected at least one dominant characteristic using a first stimulation mode; and code for generating a second stimulation signal for the received sound signal using a second stimulation mode that is different from the first stimulation mode; wherein each of the first and second stimulation mode specify a different arrangement of electrodes for current flow between the arrangement of electrodes.

20. The computer readable medium of claim 19, wherein at least two measurable characteristics of the sound signal are identified.

21. The computer readable medium of claim 20, further comprising code for selecting a distinct stimulation mode for each identified measurable characteristic, such that a unique stimulation mode is for applying each identified characteristic to the auditory nerve.

22. The computer readable medium of claim 19, further comprising code for generating stimulations in each mode with reference to a pitch map to allow for differing pitch perceptions of stimulations in each distinct stimulation mode.

23. The computer readable medium of claim 19, wherein the plurality of measurable characteristic of the sound signal comprises at least two of:

one or more unique sound sources identified in the presence of background noise;

time trajectory of a fundamental frequency (F0) of a human voice;

time trajectory of a first formant frequency (F1) of a human voice;

time trajectory of a second formant frequency (F2) of a human voice;

a quantitative metric indicating a degree of voicing of a human voice;

a quantitative metric indicating a degree of nasality of a human voice;

a quantitative metric indicating a fricative degree of a human voice; and a quantitative metric indicating an abruptness of a human voice.

24. The computer readable medium of claim 19, wherein the plurality of stimulation modes includes at least one of:

a monopolar stimulation mode;

a bipolar stimulation mode;

a tripolar mode utilizing a current flowing from one electrode to two adjacent electrodes situated either side of the one electrode; and a double monopolar mode utilizing current flowing from two intra-cochlear electrodes to one or more extra-cochlear electrodes.

* * * * *